US010254196B2

(12) United States Patent
Zhou et al.

(10) Patent No.: US 10,254,196 B2
(45) Date of Patent: Apr. 9, 2019

(54) OPTICAL FIBER CONNECTOR INSPECTOR WITH TWO-DIMENSIONAL SCANNING FUNCTION

(71) Applicant: LIGHTEL TECHNOLOGIES, INC., Renton, WA (US)

(72) Inventors: Ge Zhou, Renton, WA (US); Shangyuan Huang, Seattle, WA (US)

(73) Assignee: LIGHTEL TECHNOLOGIES, INC., Renton, WA (US)

(*) Notice: Subject to any disclaimer, the term of this patent is extended or adjusted under 35 U.S.C. 154(b) by 31 days.

(21) Appl. No.: 15/801,310

(22) Filed: Nov. 1, 2017

(65) Prior Publication Data

US 2018/0348085 A1    Dec. 6, 2018

Related U.S. Application Data

(63) Continuation-in-part of application No. 15/611,750, filed on Jun. 1, 2017, now Pat. No. 10,101,570.

(51) Int. Cl.
| | |
|---|---|
| *G01M 11/00* | (2006.01) |
| *G01N 21/88* | (2006.01) |
| *G01N 21/01* | (2006.01) |
| *G01N 21/896* | (2006.01) |
| *G02B 21/00* | (2006.01) |
| *G01N 21/95* | (2006.01) |
| *G01B 11/00* | (2006.01) |

(52) U.S. Cl.
CPC ............. *G01M 11/30* (2013.01); *G01N 21/01* (2013.01); *G01N 21/8806* (2013.01); *G01N 21/896* (2013.01); *G01N 21/95* (2013.01); *G02B 21/002* (2013.01); *G01B 11/00* (2013.01); *G01N 2021/9511* (2013.01)

(58) Field of Classification Search
CPC ...... G01M 11/30; G01M 11/00; G01N 21/01; G01N 21/8806; G01N 21/896; G01N 21/95; G01N 2021/9511; G02B 21/002; G01B 11/00
USPC ........................................................ 359/368
See application file for complete search history.

(56) References Cited

U.S. PATENT DOCUMENTS

| | | | |
|---|---|---|---|
| 6,466,366 B1 * | 10/2002 | Dominique | .......... G02B 6/3807 356/73.1 |
| 6,751,017 B2 | 6/2004 | Cassady | |
| 6,879,439 B2 | 4/2005 | Cassady | |

(Continued)

*Primary Examiner* — William R Alexander
(74) *Attorney, Agent, or Firm* — Pai Patent & Trademark Law Firm; Chao-Chang David Pai

(57) ABSTRACT

A connector inspector includes a microscope assembly, a supporting tray, a main frame, and a fitting tip. The microscope assembly is placed within the supporting tray with a bottom cylindrical protrusion inserted into a base plate of the supporting tray, and the supporting tray is coupled with the main frame with a pair of pivoting joints. The microscope assembly is horizontally biased by a spring and an adjusting knob, set between the main frame and the microscope assembly. The microscope assembly is vertically biased by a spring and an adjusting knob, set between the main frame and the microscope assembly. Thus, the microscope assembly may be swung to shift the imaging axis in two dimensions. The design of enables the inspector to be used with just one hand. See-through windows are formed on the sides of the fitting tip for monitoring the shifting of the imaging axis.

20 Claims, 11 Drawing Sheets

(56) References Cited

U.S. PATENT DOCUMENTS

| | | | |
|---|---|---|---|
| 7,336,884 B2 | 2/2008 | Zhou et al. | |
| 8,104,976 B2 | 1/2012 | Zhou et al. | |
| 9,110,252 B2 | 8/2015 | Zhou et al. | |
| 9,841,567 B1* | 12/2017 | Zhou | G02B 6/385 |
| 10,101,570 B1* | 10/2018 | Zhou | G02B 21/0036 |
| 2003/0179447 A1* | 9/2003 | Cassady | G02B 21/0016 |
| | | | 359/391 |
| 2004/0213537 A1* | 10/2004 | Villeneuve | G02B 6/3807 |
| | | | 385/134 |
| 2008/0019656 A1* | 1/2008 | Zhou | G02B 6/3833 |
| | | | 385/136 |
| 2008/0088833 A1* | 4/2008 | Yokota | G01N 21/9503 |
| | | | 356/237.5 |
| 2010/0290744 A1* | 11/2010 | Zhou | G02B 6/3833 |
| | | | 385/89 |
| 2014/0063598 A1* | 3/2014 | Zhou | G02B 6/3866 |
| | | | 359/368 |
| 2015/0092043 A1* | 4/2015 | Baribault | H04N 5/2252 |
| | | | 348/125 |
| 2017/0003195 A1* | 1/2017 | Lafrance | G01M 11/30 |

\* cited by examiner

OPTICAL FIBER CONNECTOR INSPECTOR WITH TWO-DIMENSIONAL SCANNING FUNCTION

CROSS REFERENCE TO RELATED APPLICATION

This application is a continuation-in-part application of the application Ser. No. 15/611,750, filed on Jun. 1, 2017. The entirety of said Application is incorporated herein by reference.

BACKGROUND OF THE INVENTION

1. Field of the Invention

The invention relates to fiber-optic connector inspection devices and more particularly to a connector inspector that allows the imaging axis of the microscope of the inspector to be shifted in two mutually perpendicular directions, for inspecting a fiber-optic connector having multiple rows and multiple columns of endfaces.

2. Description of the Related Art

The widespread implementation of fiber-optic communications for high-density interconnections has driven more and more multi-fiber connectors to be adopted in the industry. This creates an urgent need for regularly inspecting and maintaining the multi-fiber connectors in place, which are often situated behind backplanes or in locations which are very difficult to access.

It is well known in the fiber-optic communication industry that the endfaces of optical fibers within communication systems must be kept clean and undamaged, otherwise serious signal loss could result. The demand for cleanliness for fiber-optic endfaces has become even more stringent as the communication bandwidths increase and new communication technologies requiring higher laser power are applied.

Many types of microscopes are already available for inspecting endfaces of a fiber-optic connector to make sure the endfaces are undamaged and clean. Due to the need for sufficient magnification, the endfaces are typically inspected only one or two at a time. For a multi-fiber connector having optical fibers arranged in a single row, with the centers of the endfaces spaced typically at 0.25 mm, the microscope must be able to scan from one side to the other side of the connector in order to inspect each of the fiber-optic endfaces. Lately, multi-fiber connectors with optical fibers arranged in multiple rows (up to 6 rows and 12 optical fibers per row) have been developed and gradually adopted in the fiber-optics industry. For such multi-row fiber-optic connectors, the microscope must be able to shift its imaging axis, not only from side to side within each row but also from row to row, in order for all the endfaces to be inspected.

Cassady (U.S. Pat. Nos. 6,751,017 and 6,879,439) discloses a microscope for inspecting fiber-optic endfaces in a (single row) multi-fiber connector. The microscope comprises a slider assembly, a slider chassis and a drive assembly, in which the driver assembly interfaced with the slider assembly is capable of selectively displacing the slider chassis along an axis of motion to selectively direct the imaging axis of the microscope between adjacent fiber-optic endfaces.

U.S. Pat. No. 7,336,884 (to Zhou et al.) provides an adaptive device for inspecting fiber-optic endfaces arranged in a single row through the microscope. The device comprises a supporting body; a pendular arm rotatably mounted to the supporting body; a fitting tip attached to the pendular arm; and a bevel wheel fastened to the supporting body. The bevel wheel is adapted to swing the pendular arm relative to the supporting body so that the imaging axis of the microscope is shifted relative to the fitting tip to selectively align with the endfaces for inspection. However, with this device, the imaging axis of the microscope moves along a circular track relative to the fitting tip and may not be aligned with the center of some of the endfaces in a (single-row) multi-fiber connector.

U.S. Pat. No. 8,104,976 to Zhou et al. discloses an improved adaptive device for shifting the imaging axis of the microscope in a straight line over the endfaces of a single-row multi-fiber connector for inspecting the endfaces. The adaptive device is capable of bringing each endface of the multi-fiber connector into the field of view of the microscope for inspection. More specifically, the adaptive device comprises an adjustment driver and a swinging lever connected to a fitting tip, wherein the adjustment driver is adapted to swing the optical tube of the microscope relative to the swinging lever, thereby selectively shifting the imaging axis of the microscope relative to the fitting tip along a straight-line over the endfaces of a single-row multi-fiber connector interfaced with the fitting tip.

U.S. Pat. No. 9,110,252 to Zhou et al. discloses an adaptive device for shifting the imaging axis of a microscope in two mutually perpendicular directions for inspecting a fiber-optic connector having multiple rows of endfaces. FIG. 1 shows such an adaptive device 6 to be used with a conventional inspector 5, an MTP/MPO connector adapter 8 and an MTP/MPO connector 7 in relative connecting positions. The adaptive device 6 is connected with the MTP/MPO connector adapter 8 by inserting a front fitting tip 68 into the front-side mouth 86 of a channel in the MTP/MPO connector adaptor 8. The front part 78 of the MTP/MPO connector 7 is inserted into the back-side mouth 87 of the channel. The adaptive device 6 has a rear opening 65 adapted for receiving the front end 56 of the inspector 5. Therefore, the imaging axis 501 of the microscope in the inspector 5 extends from inside the inspector 5, through the adaptive device 6 and the front-side mouth 86 of the connector adapter 8 to intersect the ferrule surface 71 of the connector 7. In short, by using a first swinging lever rotatable about a first swinging axis perpendicular to the imaging axis of the microscope, a second swinging lever rotatable about a second swinging axis perpendicular to the first swinging axis, and two sets of biasing means and adjustment drivers actuated by the two adjustment knobs 63,64, the adaptive device 6 allows the imaging axis 501 passing through it to be shifted in two mutually perpendicular directions so that it may be selectively aligned with any endface of the connector 7. However, because the adaptive device 6 is connected to the front end 56 of the inspector 5, and the two adjustment knobs 63,64 are not adjacent to the focusing knob 57 of the inspector 5, the user must use both hands to operate the inspector 5 and the adaptive device 6, namely, one hand holding the inspector 5 and the other tuning the adjustment knobs 63,64.

In view of the foregoing, a more flexible and user-friendly connector inspector with two-dimensional scanning function for the imaging axis of the inspection microscope is needed and will be particularly useful in inspecting multi-fiber connectors commonly found in the communication systems these days.

BRIEF SUMMARY OF THE INVENTION

This invention provides an optical fiber connector inspector for shifting the imaging axis of the microscope in the connector inspector in two mutually perpendicular directions relative to the ferrule surface of a fiber-optic connector to selectively align the imaging axis with each of the endfaces for inspection. The connector inspector is different from the prior art connector inspector equipped with an external adaptive device in that the two-dimensional scanning function is directly built into the inspector body instead of using an external adaptive device to provide the two-dimensional function for the inspector.

The optical fiber connector inspector with two-dimensional scanning function includes a core module assembled from a microscope assembly, a supporting tray, and a main frame.

The microscope assembly has a tubular front portion with an axis collinear with the imaging axis of the microscope assembly. The microscope assembly is placed upon a base plate and within a receiving space between two side plates of the supporting tray, with a bottom cylindrical protrusion inserted into a through hole in the base plate of the supporting tray. While the bottom surface of the microscope assembly is kept in contact with the base plate of the supporting tray, the microscope assembly is allowed to swing left or right, along with the tubular front portion and therefore the imaging axis, on the axis of the bottom cylindrical portion that extends upwards through a first recess formed in a top surface of the microscope assembly.

Two side plates of the supporting tray are respectively connected to two side plates of the rear portion of the main frame by two pivoting joints, whereby the pivoting joints serve as an axis on which the supporting tray with the microscope assembly thereupon may swing up or down relative to the main frame, causing the tubular front portion and therefore the imaging axis to also swing up or down.

The left-or-right swinging of the microscope assembly within the receiving space of the supporting tray is biased simultaneously by a spring disposed at a second recess formed in one side surface of the microscope assembly and by the thread rod of an X-direction scanning knob pushing on the other side surface of the microscope assembly. The X-direction scanning knob is disposed on the corresponding side plate of the rear portion of the main frame and may be turned to control the extent to which the microscope assembly is swung left or right.

The up-or-down swinging of the microscope assembly with the supporting tray relative to the main frame is biased simultaneously by a spring disposed at the first recess formed in the top surface of the microscope assembly and by the thread rod of an Y-direction scanning knob pushing on the top surface of the microscope assembly. To achieve that, the plane containing the axis formed by the two pivoting joints and perpendicular to the top surface of the microscope assembly should pass between the thread rod of the Y-direction scanning knob and the spring at the first recess. The Y-direction scanning knob is disposed on the top plate of the rear portion of the main frame and may be turned to control the extent to which the microscope assembly is swung up or down.

Preferably, the connector inspector of the present invention is constructed such that the imaging axis of the microscope assembly always perpendicularly intersects the axis on which the microscope assembly is swung left or right, and that at an initial position, the imaging axis of the microscope assembly is also perpendicular to the axis on which the microscope assembly is swung up or down. When the connector inspector is interfaced with a connector, e.g. through a fitting tip thereof and a connector adapter, the imaging axis of the microscope assembly initially will intersect the ferrule surface of the connector at the right angle. When the microscope assembly is swung left or right, the imaging axis will be shifted in a direction parallel to an X-axis of the coordinate system defined for the ferrule surface of the connector. On the other hand, when the microscope assembly is swung up or down, the imaging axis will be shifted in a direction parallel to an Y-axis of the coordinate system defined for the ferrule surface of the connector. Therefore, with the connector inspector of the present invention, individual fiber-optic endfaces of the connector may be focused and aligned with the imaging axis for effective inspection with just one hand.

Finally, the fitting tip of the connector inspector may have see-through windows formed on its sides, allowing the user to monitor the angle and position of the tubular front portion of the microscope assembly inside the connector inspector.

DETAILED DESCRIPTION OF THE INVENTION

Figure 1:
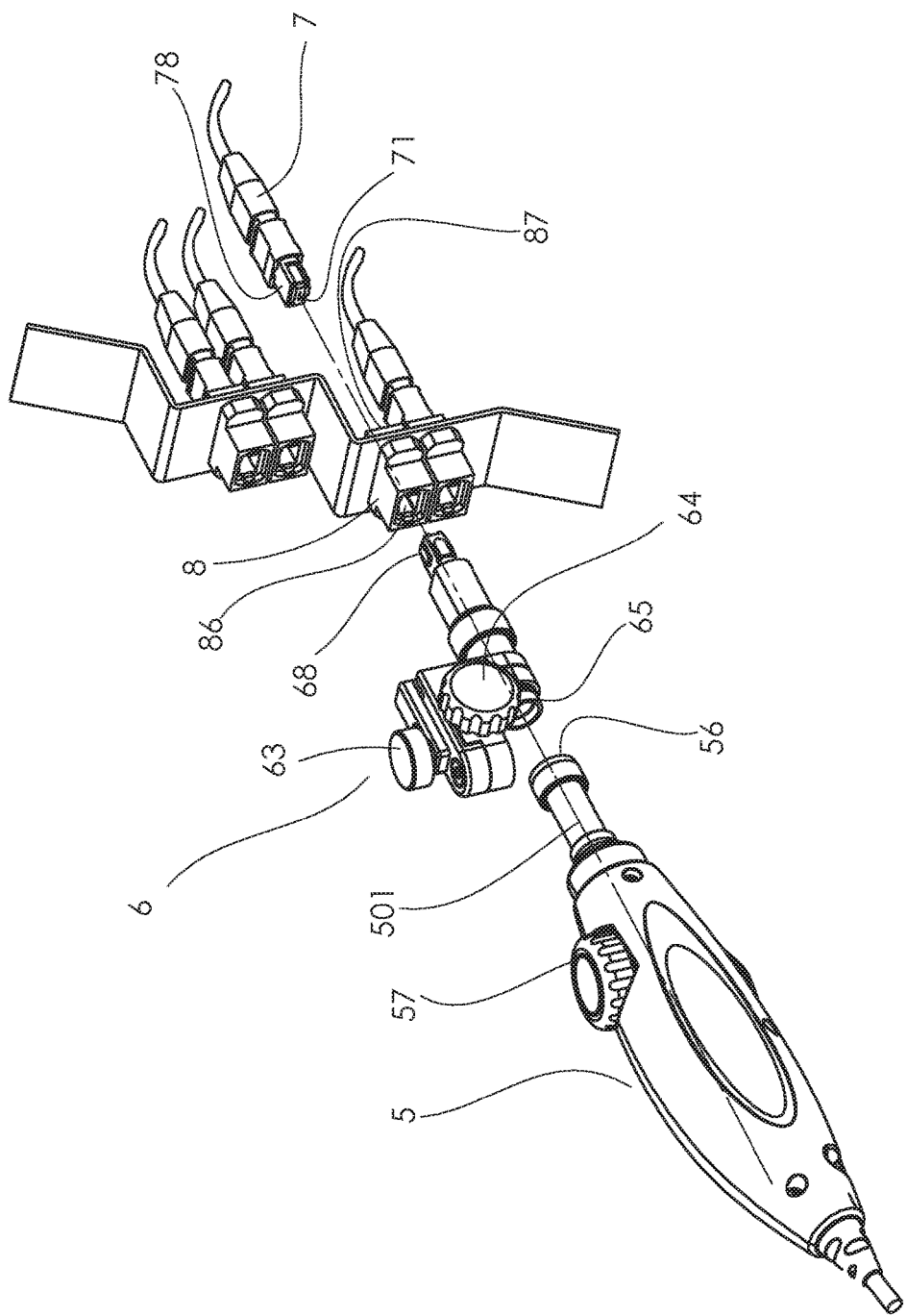
FIG. 1 shows a prior art adaptive device for shifting the imaging axis of the inspector microscope in two mutually perpendicular directions.
Figure 2:
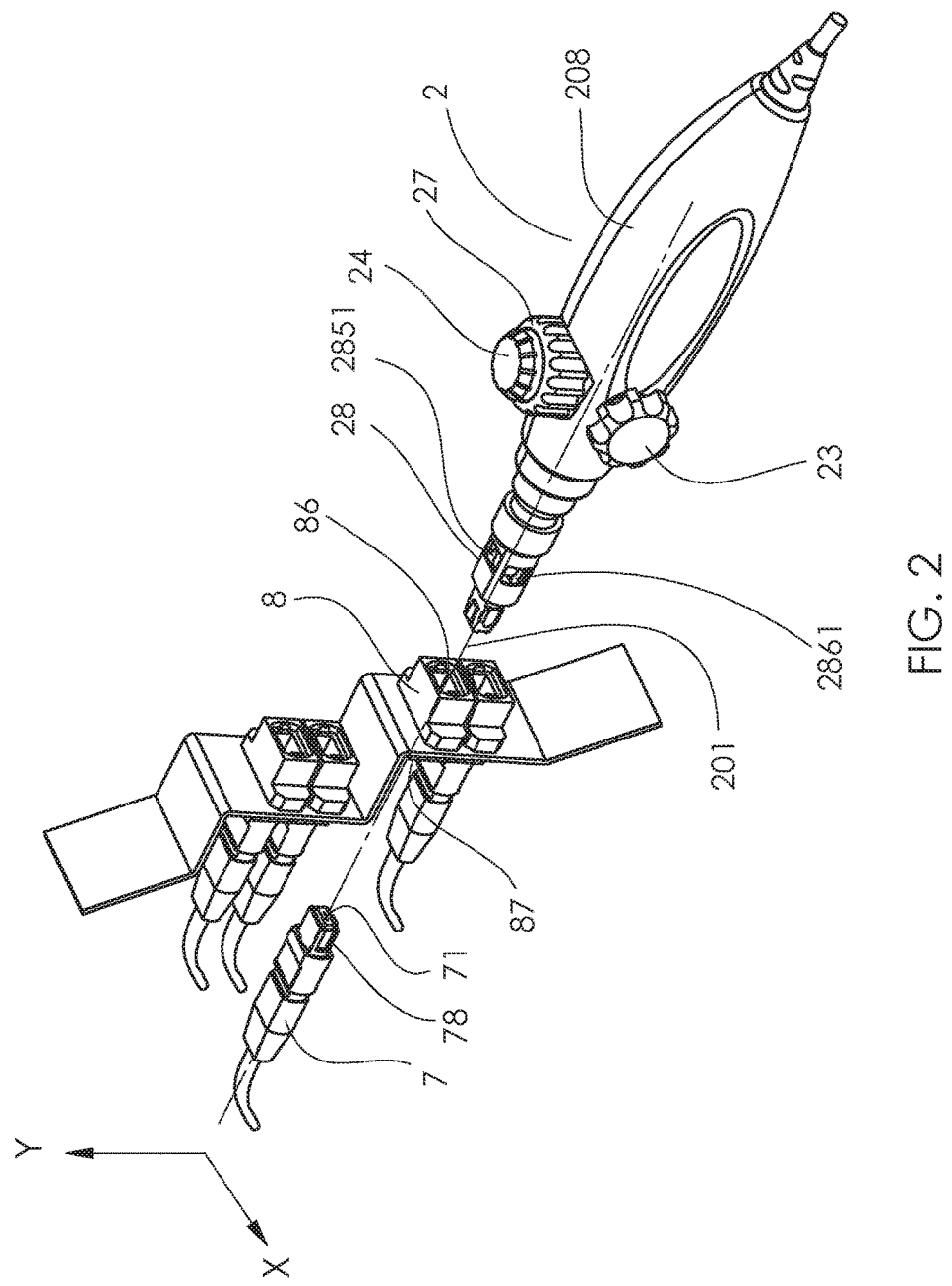
FIG. 2 shows the connector inspector according to the present invention in relative connecting position with a connector adapter and a connector.

FIG. 2 illustrates the fiber-optic connector inspector 2 according to a preferred embodiment of the present invention for shifting the imaging axis 201 of a microscope assembly 22 (see FIG. 3) embedded in the connector inspector 2 in two mutually perpendicular directions for inspecting the endfaces of a multi-fiber connector 7 having multiple rows of multiple endfaces. The multi-fiber connector 7 is usually an MTP or MPO connector. In FIG. 2, the inspector 2 is coupled with the multi-fiber connector 7 through an MTP/MPO connector adaptor 8, wherein a fitting tip 28 of the inspector 2 is inserted into the front-side mouth 86 of a channel in the MTP/MPO connector adaptor 8, and the front part 78 of the MTP/MPO connector 7 is inserted into the back-side mouth 87 of the channel. As illustrated in FIG. 2, the inspector 2 has an X-direction scanning knob 23, a Y-direction scanning knob 24, and a focusing knob 27 surrounding the Y-direction scanning knob 24 for adjusting the focal length of the microscope assembly 22. Essentially, with the inspector 2 according to the present invention, a user turns the X-direction scanning knob 23 to shift the imaging axis 201 of the microscope assembly 22 in an X-direction (which is preferably set to be parallel to the longer side of the front-side mouth 86 of the connector adaptor 8, or equivalently, parallel to the longer side of the ferrule surface 71 of the connector 7), and turns the Y-direction scanning knob 24 to shift the imaging axis 201 in the Y-direction (preferably set to be perpendicular to the longer side of the ferrule surface 71 of the connector 7). Due to the relative locations of the X-direction scanning knob 23, the Y-direction scanning knob 24, and the focusing knob 27, while holding the outer shell 208 of the inspector 2 with one hand, the user can easily reach and turn the two scanning knobs 23, 24 and the focusing knob 27 with the thumb and the index finger of the same hand, thus leaving the other hand to do other tasks at the same time. Because the structure and mechanism of the focusing knob 27 of an inspection microscope is well known in the related art, it will not be further described in this application.

Figure 3:
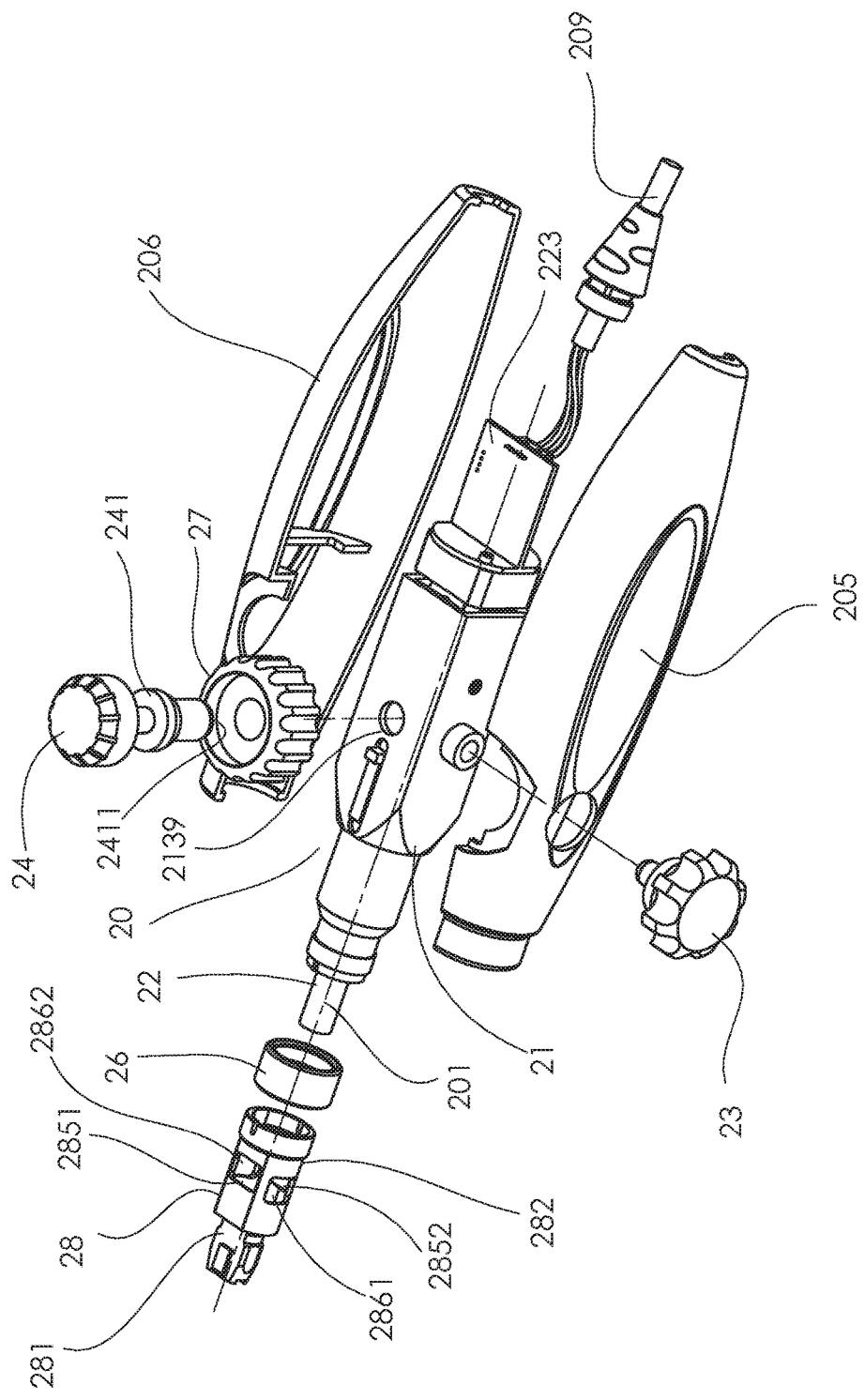
FIG. 3 is an exploded view of the connector inspector according to the present invention.
Figure 4:
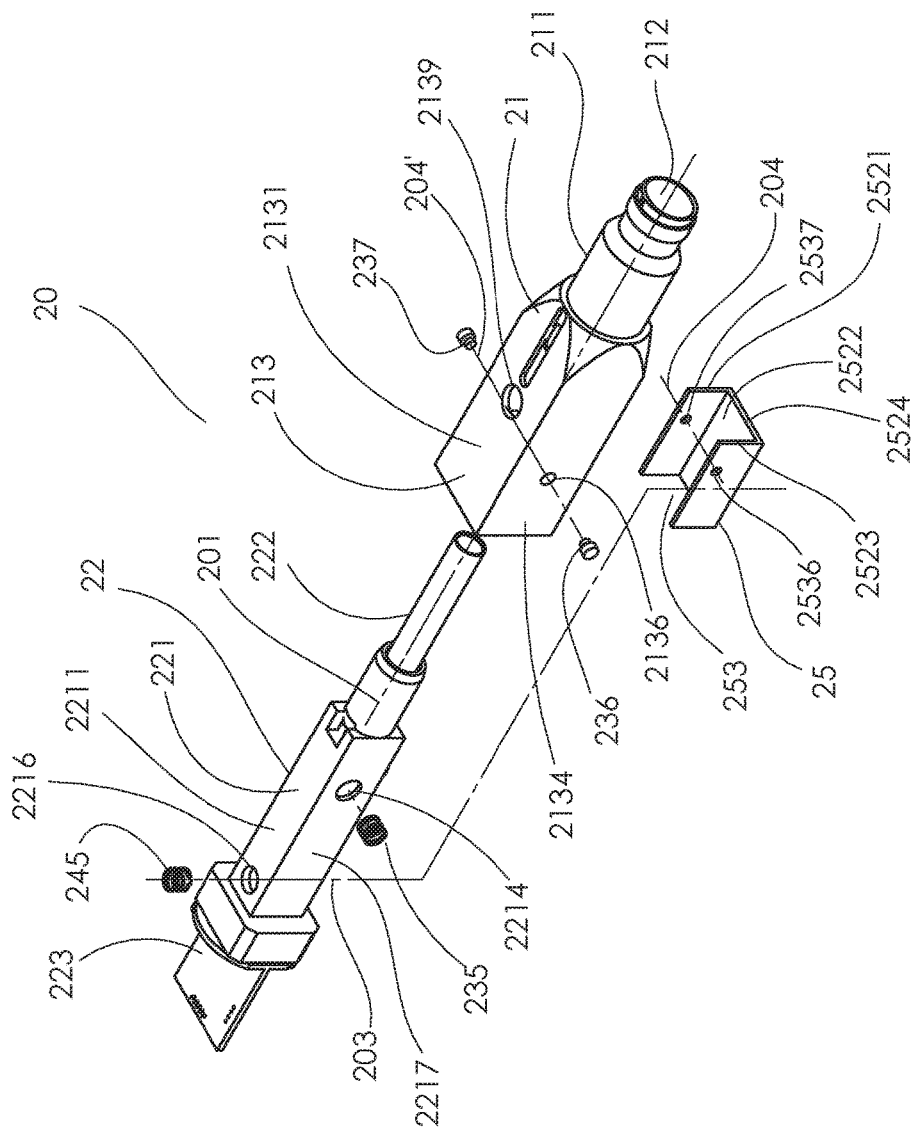
FIG. 4 is a top exploded view of the core module of the connector inspector according to the present invention.
Figure 5:
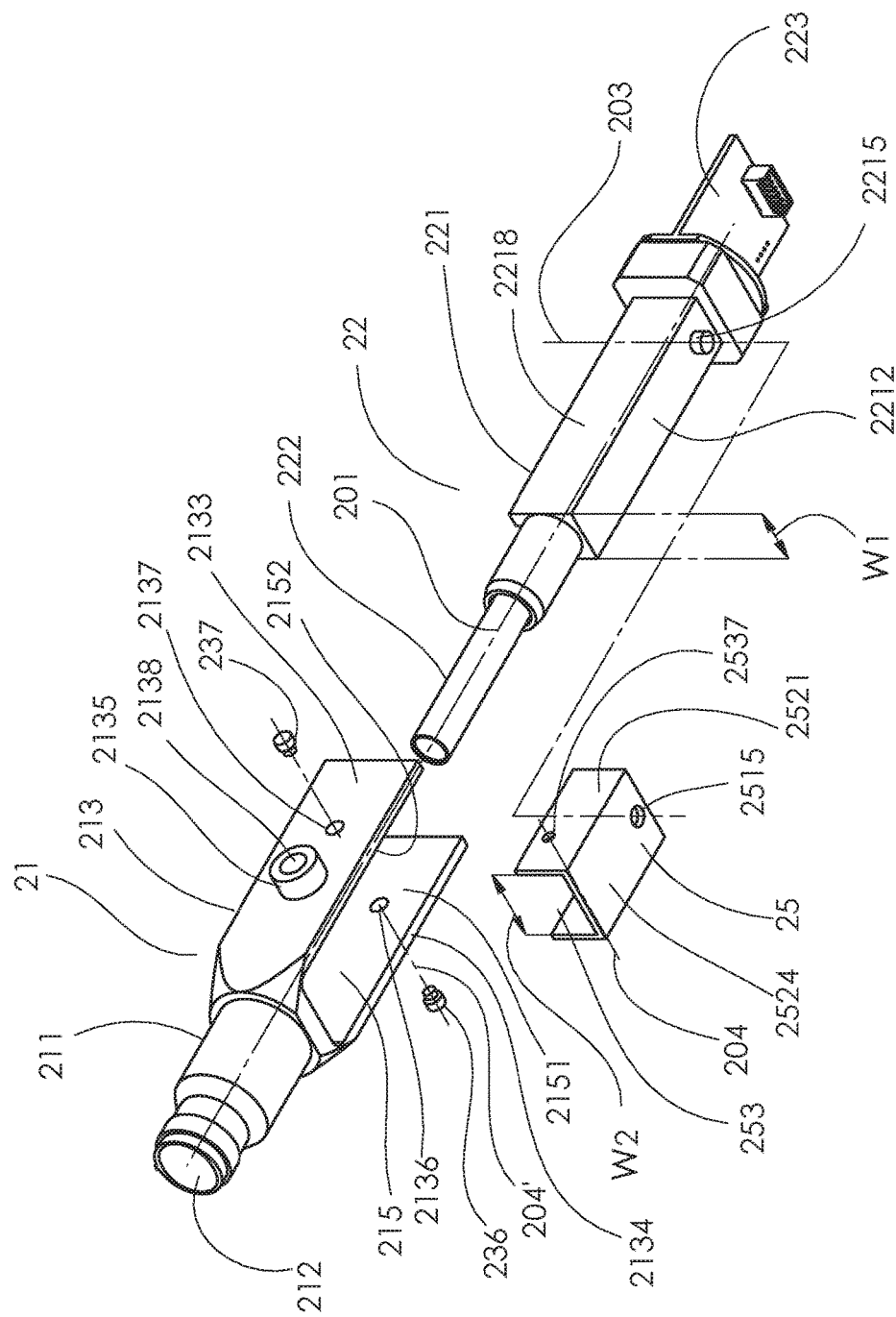
FIG. 5 is a bottom exploded view of the core module of the connector inspector according to the present invention.

FIG. 3 is an exploded view of the inspector 2 according to the present invention. The inspector 2 includes an outer shell 208 (consisting of a left half shell 205 and a right half shell 206), a microscope assembly 22, a supporting tray 25 (see FIG. 4), a main frame 21, a fitting tip 28, an annular coupler 26, and the X-direction scanning knob 23, the Y-direction scanning knob 24 and the focusing knob 27 previously mentioned. The microscope assembly 22, the supporting tray 25, and the main frame 21 are assembled together to form a core module 20 of the inspector 2. The core module 20 is covered and protected by the outer shell 208, which is fixed to the main frame 21. FIG. 4 and FIG. 5 are exploded views of the core module 20 of the inspector 2.

Generally speaking, the type of the fitting tip 28 depends upon the type (e.g. physical contact or angular physical contact) of the connector 7 to be inspected. The fitting tip 28 will be described in more detail later.

As illustrated in FIG. 4 and FIG. 5, the microscope assembly 22 includes a tubular front portion 222, a rear housing portion 221, and optionally a camera 223 attached to the rear side of the rear housing portion 221 for taking images of the connector endfaces being inspected. The microscope assembly 22 may also include a cable 209 (see FIG. 3) attached to the camera 223 for transmitting images taken by the camera 223 to another device (not shown), such as a monitor or a computer. The tubular front portion 222 has an axis collinear with the imaging axis 201 of the microscope assembly 22. The rear housing portion 221 has a top surface 2211, a bottom surface 2212, a first side surface 2217 and a second side surface 2218. Moreover, a round first recess 2216 is formed in the top surface 2211 at equal distance from the two side surfaces 2217,2218, a round second recess 2214 is formed in the first side surface 2217, and a cylindrical protrusion 2215 is formed on the bottom surface 2212 at equal distance from the two side surfaces 2217,2218. Preferably, the first recess 2216 and the cylindrical protrusion 2215 are positioned such that the axis 203 of the cylindrical protrusion 2215 is perpendicular to the bottom surface 2212 and extends through the center point of the first recess 2216 and perpendicularly intersects the imaging axis 201 of the microscope assembly 22. The first recess 2216 is designed to receive one end of a first elastic member 245, and the second recess 2214 is designed to receive one end of a second elastic member 235. The function of the first elastic member 245 and the second elastic member 235, each of which is preferably a spiral spring, will be explained later.

In the embodiment illustrated in FIG. 4 and FIG. 5, both the top surface 2211 and the bottom surface 2212 are flat and parallel to each other, both the first side surface 2217 and the second side surface 2218 are flat and perpendicular to the top surface 2211 (and to the bottom surface 2212). However, that is not required for the connector inspector 2 of the present invention to function properly.

As illustrated in FIG. 4 and FIG. 5, the supporting tray 25 has a base plate 2524 with a top surface 2522 and two side plates 2521,2523, thus defining a receiving space 253 between the two side plates 2521,2523 and above the base plate 2524. Moreover, a bottom through hole 2515 is formed in the base plate 2524 spaced from the two side plates 2521,2523, and two side through holes 2537,2536 are respectively formed in the two side plates 2521,2523. In one embodiment of the connector inspector 2 of the present invention, the two side plates 2521,2523 are both flat and parallel to each other, such that an axis 204 extending through respective centers of the two side through holes 2537,2536 is perpendicular to the two side plates 2521,2523 of the supporting tray 25. The top surface 2522 of the base plate 2524 of the supporting tray 25 may also be flat to flushly contact the bottom surface 2212 of the rear housing portion 221 of the microscope assembly 22.

As illustrated in FIG. 4 and FIG. 5, the main frame 21 has a tubular front portion 211 and a rear portion 213. The tubular front portion 211 is adapted for coupling to the fitting tip 28, for example, by an annular coupler 26 (as shown in FIG. 3) for interfacing with the connector 7 to be inspected. The rear portion 213 has a top plate 2131, a first side plate 2133 with an inner surface 2152, a second side plate 2134 with an inner surface 2151, and a receiving space 215 defined between the inner surfaces 2152,2151 of the two side plates 2133,2134 and below the top plate 2131. An internal channel 212 of the tubular front portion 211 is in communication with the receiving space 215. Moreover, a first threaded through hole 2138 is formed in the first side plate 2133 and a second threaded through hole 2139 is formed in the top plate 2131. As will be discussed later, the first threaded through hole 2138 is designed for installing the X-direction scanning knob 23, and the second threaded through hole 2139 is designed for installing the Y-direction scanning knob. In addition, two side through holes 2137, 2136 are respectively formed in the first side plate 2133 and the second side plate 2134 such that an axis 204' extending through respective centers of the two side through holes 2137,2136 is perpendicular to the two side plates 2133,2134.

Figure 10:
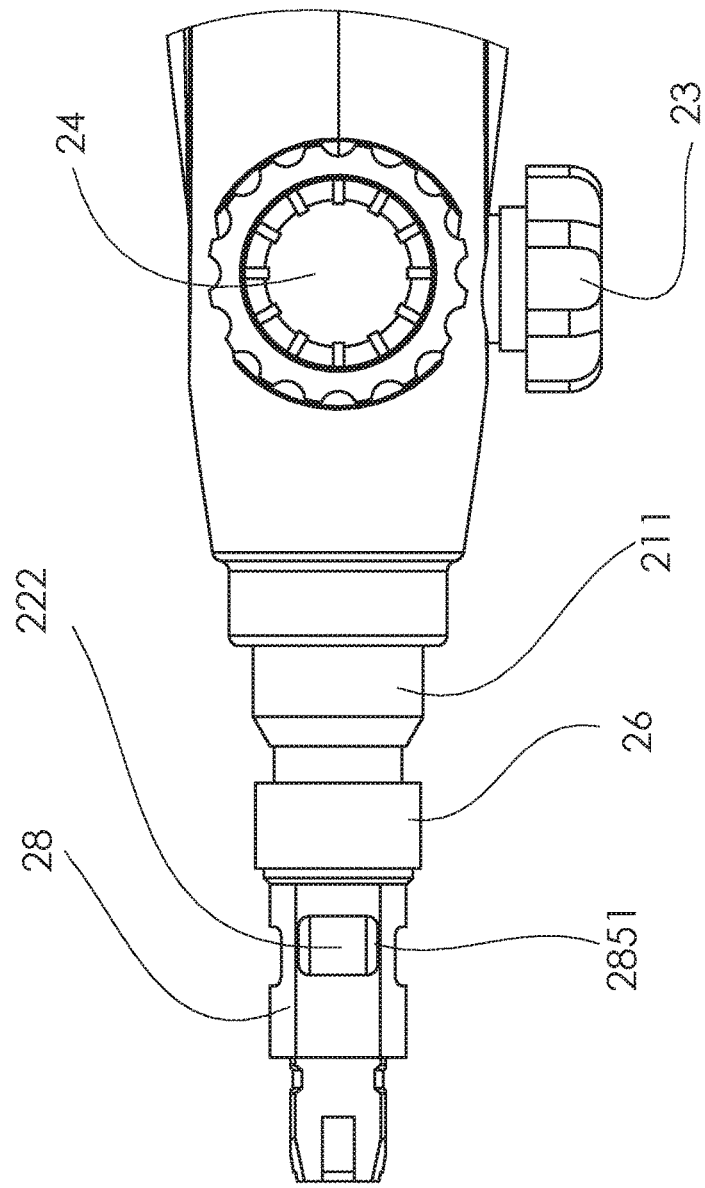
FIG. 10 shows a see-through window formed on the top side of the fitting tip of the connector inspector of the present invention.
Figure 11:
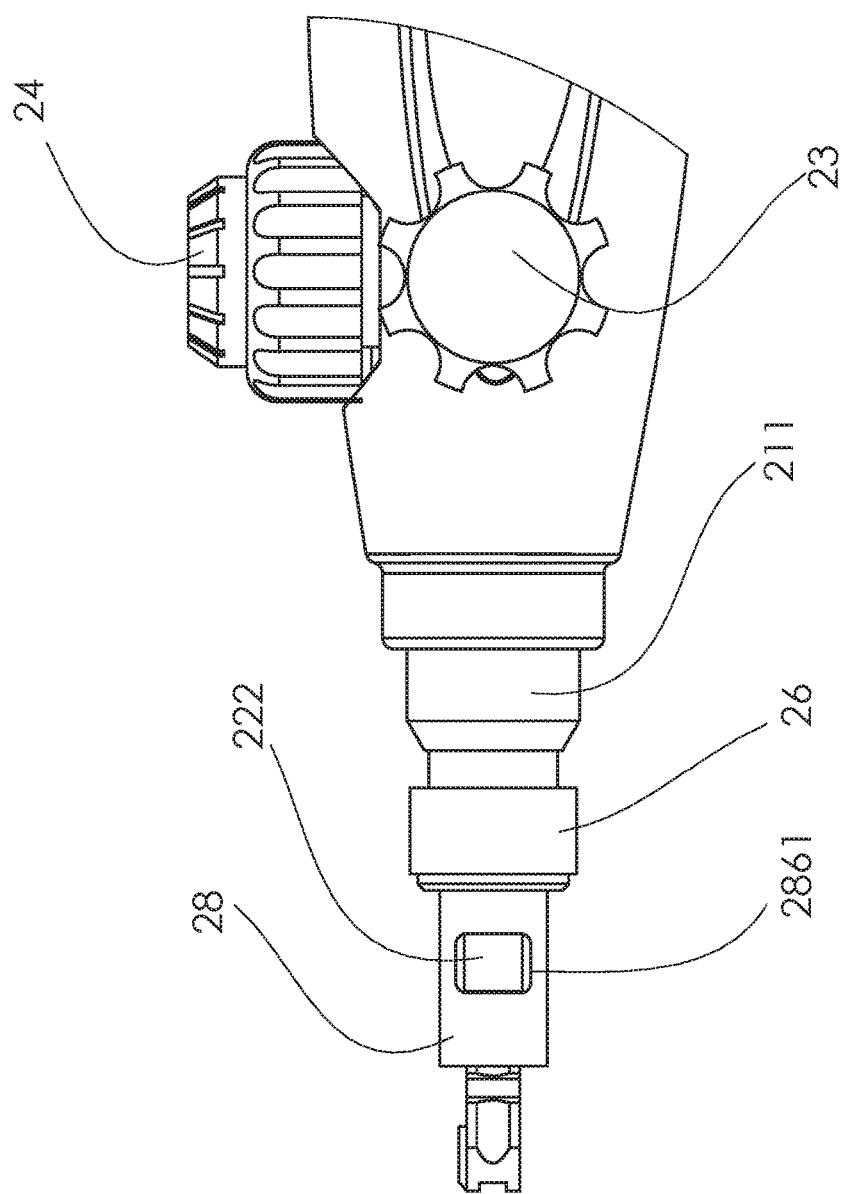
FIG. 11 shows a see-through window on the left side of the fitting tip of the connector inspector of the present invention.

As illustrated in FIG. 2 and FIG. 3, the fitting tip 28 has a front insertion portion 281 and a rear portion 282. The front insertion portion 281 is for inserting into a connector adapter 8 to interface with a connector 7. The rear portion 282 is for coupling with the tubular portion 211 of the main frame 21. When so coupled, a front section of the tubular front portion 222 of the microscope assembly 22 extends into the rear portion 282. The rear portion 282 of the fitting tip 28 may have two see-through windows 2851, 2852 on the top and bottom sides thereof, respectively, and two see-through windows 2861, 2862 on two lateral sides thereof. FIG. 10 shows an enlarged top view of the see-through window 2851. and FIG. 11 shows an enlarged side view of the see-through window 2861. These see-through windows allow the user to monitor the position and angle of the tubular front portion 222 of the microscope assembly 22 extending into the rear portion 282 of the fitting tip 28. In fact, for the user to monitor the horizontal position and angle of the tubular front portion 222, just one see-through window 2851 or 2852 on the fitting tip 28 is needed. Similarly, for the user to monitor the vertical position and angle of the tubular front portion 222, just one see-through window 2861 or 2862 on the fitting tip 28 is needed. Certainly, it is more convenient to have all four windows on the fitting tip 28.

Figure 6:
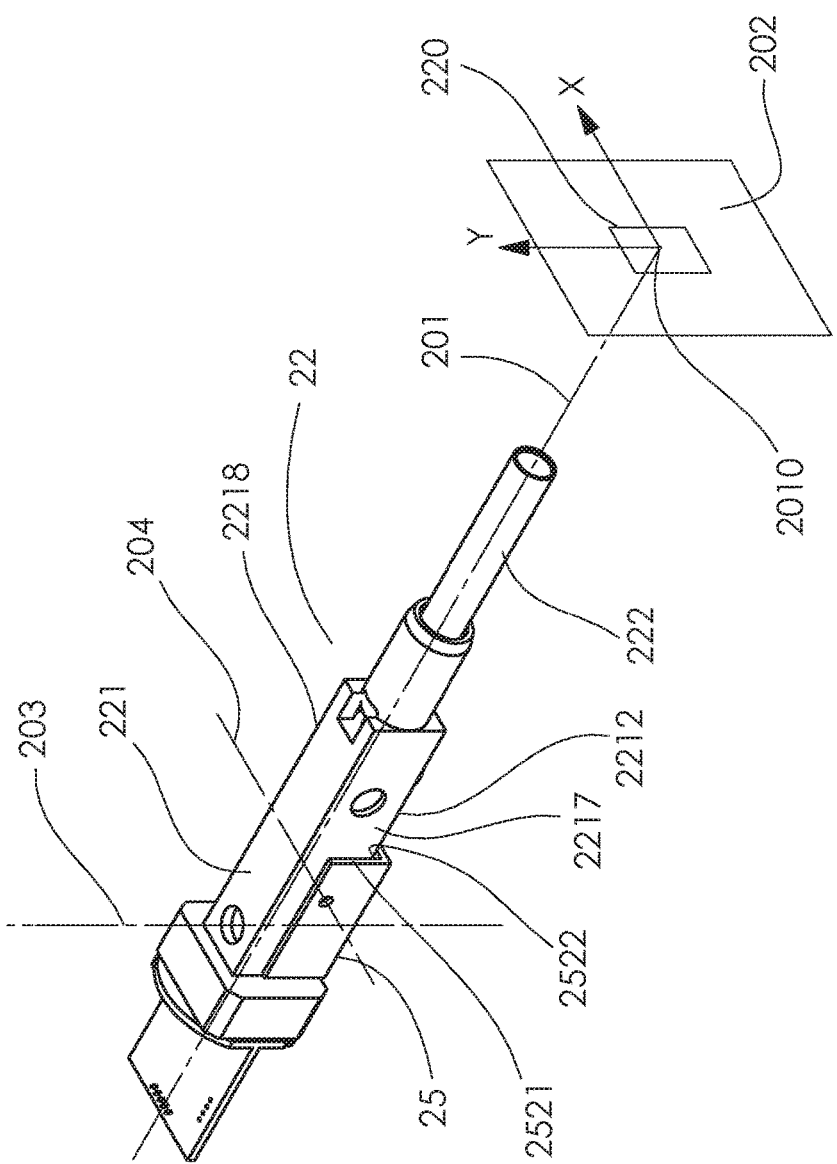
FIG. 6 illustrates the relationship between the imaging axis and the two mutually perpendicular axes on which the imaging axis of the connector inspector of the present invention may be caused to swing.
Figure 7:
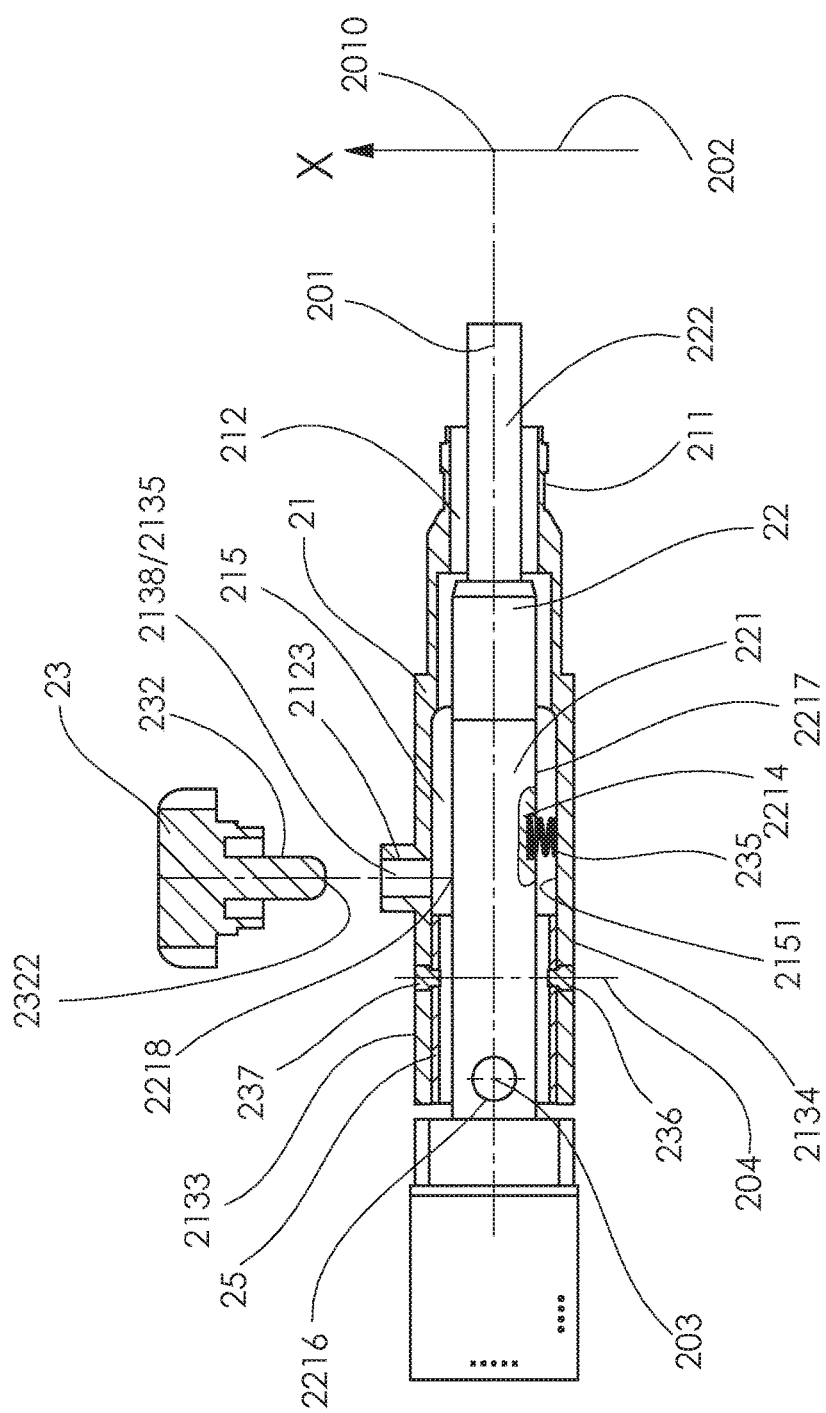
FIG. 7 is a partial cross-sectional view illustrating the mechanism of the scanning function in the X-direction of the connector inspector of the present invention.
Figure 8:
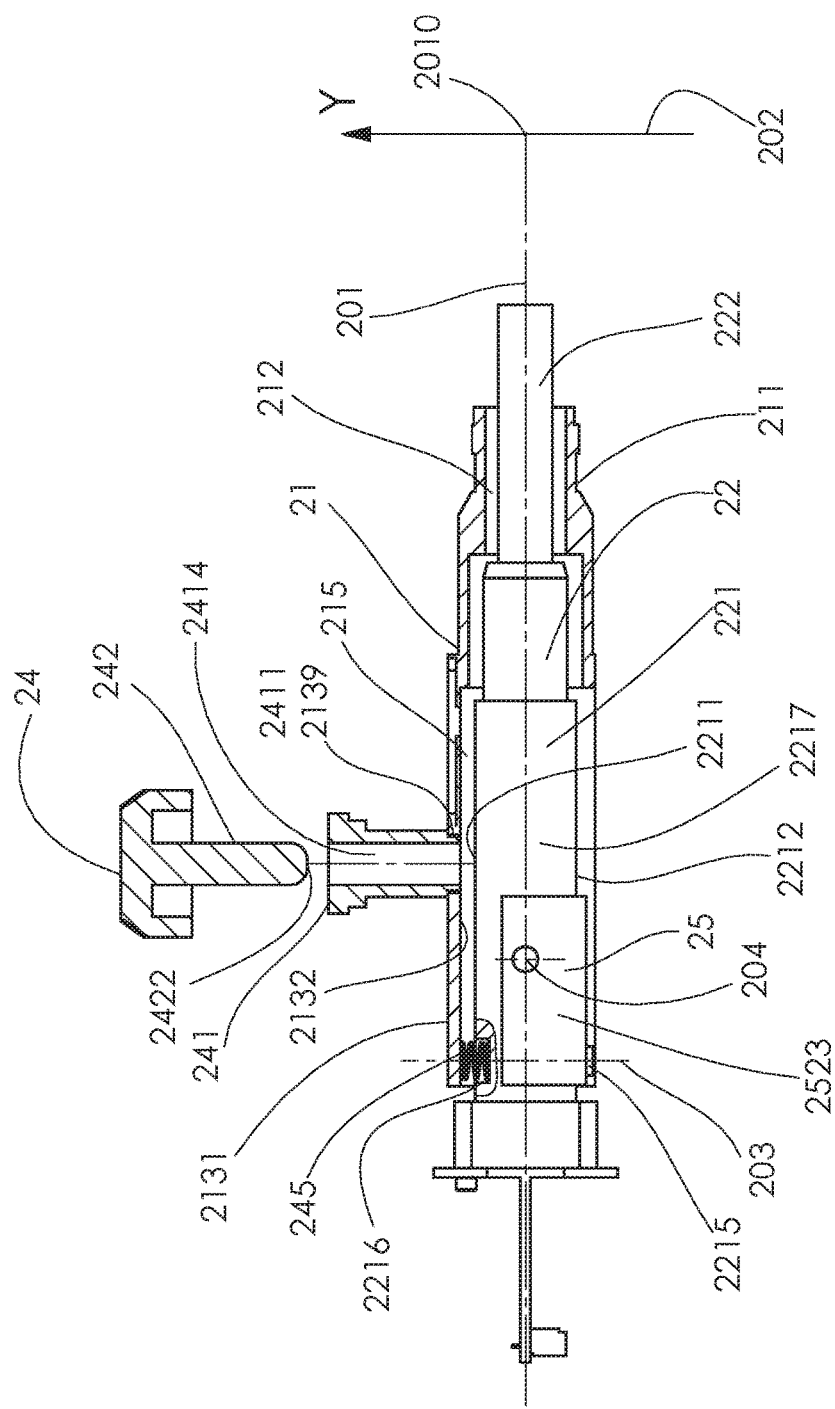
FIG. 8 is a partial cross-sectional view illustrating the mechanism of the scanning function in the Y-direction of the connector inspector of the present invention.

FIGS. 6-8 illustrate how the components of the core module 20 of the inspector 2 are assembled together and how the assembled inspector 2 works to allow two-dimensional scanning of the ferrule surface 71 by shifting the imaging axis 201. FIG. 6 shows that a rear section of the rear housing portion 221 is placed within the receiving space 253 of the supporting tray 25, such that the two side surfaces 2217,2218 of the rear housing portion 221 are respectively spaced from the two side plates 2523,2521 of the supporting tray 25, and the cylindrical protrusion 2215 of the rear housing portion 221 is fittingly inserted into the bottom through hole 2515 in the base plate 2524 of the supporting tray 25. Essentially, the bottom through hole 2515 in the base plate 2524 of the supporting tray 25 serves as a bushing for the cylindrical protrusion 2215 of the rear housing portion 221 to turn therein. Furthermore, a rear section of the bottom surface 2212 of the rear housing portion 221 contacts the top surface 2522 of the base plate 2524 of the supporting tray 25 from above. As a result, the axis 203 of the cylindrical protrusion 2215 passes through the center of the bottom through hole 2515 of the supporting tray 25 and is perpendicular to the top surface 2522 of the base plate 2524 of the supporting tray 25. Thus, the microscope assembly 22 may swing on the axis 203 relative to the supporting tray 25 to the extent permitted by the width of the receiving space 253 of the supporting tray 25. Therefore, the axis 203 serves as the first axis of rotation (also denoted as 203) for the microscope assembly 22 to shift the imaging axis in one of the two dimensions. FIG. 6 shows that the imaging axis 201 of the microscope assembly 22 perpendicularly intersects the object plane 202 at a point 2010 at the center of the field of view 220. This occurs when the microscope assembly 22 is symmetrically placed in the receiving space 253 of the supporting tray 25, i.e., with the two side surfaces 2217,2218 of the rear housing portion 221 parallel to the two side plates 2523,2521 of the supporting tray 25. When the microscope assembly 22 swings on the first axis of rotation 203 relative to the supporting tray 25, the imaging axis 201 will swing along and shift the field of view 220 and the intersection point 2010 in a direction parallel to the X-axis. As shown in FIG. 5, the width $W_1$ of the rear housing portion 221 is the distance between the first side surface 2217 and the second side surface 2218, and the width $W_2$ of the receiving space 253 of the supporting tray 25 is the distance between the inner surfaces of the two side plates 2521,2523. It is obvious that for the inspector 2 to work, the width $W_2$ must be sufficiently greater than the width $W_1$.

As will be explained below in conjunction with FIG. 7 and FIG. 8, the imaging axis 201 may be shifted in a direction parallel to the X-axis by causing the microscope assembly 22 to swing on the axis 203 relative to the supporting tray 25. Furthermore, the imaging axis 201 may be shifted in a direction parallel to the Y-axis by causing the microscope assembly 22 to swing together with the supporting tray 25 on the axis 204/204'.

The microscope assembly 22 and the supporting tray 25 are mounted in the main frame 21 as described below. The tubular front portion 222 of the microscope assembly 22 is inserted through the internal channel 212 of the tubular front portion 211 of the main frame 21 with a front section of the tubular front portion 222 further extending into the rear portion 282 of the fitting tip 28; the rear housing portion 221 of the microscope assembly 22 and the supporting tray 25 are disposed in the receiving space 215 of the main frame 21; then the main frame 21 and the supporting tray 25 are jointed together by two pivoting joints 236,237 respectively inserting first through the two side through holes 2136,2137 of the rear portion 213 of the main frame 21 and then through the two side through holes 2536,2537 of the supporting tray 25. When the supporting tray 25 is mounted in the main frame 21, the axis 204 of the supporting tray 25 is collinear with the axis 204' of the main frame 21, thus defining a second axis of rotation for the microscope assembly 22, also denoted by 204. In other words, the two pivoting joints 236, 237 provide the pivot for the microscope assembly 22 (together with the supporting tray 25) to swing on the second axis of rotation 204 relative to the main frame 21. It should be noted that the second axis of rotation 204 is perpendicular to the first axis of rotation 203. More precisely, since the first axis of rotation 204 and the second axis of rotation 204 are not coplanar, they are orthogonal to each other.

In the particular embodiment illustrated in FIG. 4 and FIG. 5, the side through holes 2136,2137 of the rear portion 213 of the main frame 21 has a larger diameter than the side through holes 2536,2537 of the supporting tray 25; each of the pivoting joints 236, 237 is a stepped cylinder having a first part of a smaller diameter fittingly inserted into a side through hole (2536 or 2537) of the supporting tray 25 and a second part of a larger diameter fittingly inserted into a corresponding side through hole (2136 or 2137) of rear portion 213 of the main frame 21. However, this feature of having side through holes of different diameters is not required of the inspector 2 of the present invention. Nor is the present invention limited to this particular shape of the pivoting joints 236,237. Other forms of pivoting joints will work as long as they can pivotally couple the main frame 21 and the supporting tray 25 together.

FIG. 7 is a partial cross-sectional view illustrating the mechanism of the scanning function of the inspector 2 in the X-direction. To enable the imaging axis 201 of the microscope assembly 22 to smoothly and stably shift in the X-direction, the second elastic member 235 is set between the second recess 2214 in the first side surface 2217 of the rear housing portion 221 and the inner surface 2151 of the second side plate 2134 of the rear portion 213 of the main frame 21. Namely, the second elastic member 235 has one end received in the second recess 2214 and the other end contacting and exerting elastic force on the inner surface 2151 of the second side plate 2134 of the rear portion 213 of the main frame 21. Alternatively, the second elastic member 235 may have one end attached to the first side surface 2217 of the rear housing portion 221 without a recess formed therein. Moreover, the X-direction scanning knob 23 has a thread rod 232 screwed into the first threaded through hole 2138 of the rear portion 213 of the main frame 21 for the front tip 2322 of the thread rod 232 to contact the second side surface 2218 of the rear housing portion 221 of the microscope assembly 22. With this arrangement, as shown in FIG. 7, when the X-direction scanning knob 23 is turned to move the thread rod 232 forward, the microscope assembly 22 will be pushed (against the second elastic member 235) to swing on the first axis of rotation 203 clockwise, as viewed from the top, relative to the main frame 21, thus allowing the imaging axis 201 to shift in the negative X direction. Conversely, when the X-direction scanning knob 23 is turned to move the thread rod 232 backward, the microscope assembly 22 will be pushed back by the second elastic member 235 to swing on the first axis of rotation 203 counterclockwise relative to the main frame 21, thus allowing the imaging axis 201 to shift in the positive X direction.

As shown in FIG. 7, when the microscope assembly 22 is aligned with the side surfaces 2217,2218 parallel to the side plates 2523,2521 of the supporting tray 25, the imaging axis 201 is perpendicular to the ferrule surface 71 (i.e. the object plane 202), and the second axis of rotation 204 should be parallel to the X-axis defined for the ferrule surface 71. However, when the microscope assembly 22 is swung away from this central position, the imaging axis 201 will be slightly shifted from being perpendicular to the ferrule surface 71.

FIG. 8 is a partial cross-sectional view illustrating the mechanism of the scanning function of the inspector 2 in the Y-direction. To enable the imaging axis 201 to smoothly and stably shift in the Y-direction, the first elastic member 245 is set between the first recess 2216 in the top surface 2211 of the rear housing portion 221 of the microscope assembly 22 and the bottom surface 2132 of the top plate 2131 of the rear portion 213 of the main frame 21. Namely, the first elastic member 245 has one end received in the first recess 2216 and the other end contacting and exerting elastic force on the bottom surface 2132 of the top plate 2131 of the rear portion 213 of the main frame 21 from below. Alternatively, the first elastic member 245 may have one end attached to the top surface 2211 of the rear housing portion 221 without a recess formed therein. Moreover, the Y-direction scanning knob 24 attached to the second threaded through hole 2139 has a thread rod 242 extending through the second threaded through hole 2139 for the front tip 2422 of the thread rod 242 to contact the top surface 2211 of the rear housing portion 221 of the microscope assembly 22. The second axis of rotation 204 is preferably positioned at a level to for it to intersect the imaging axis 201 of the microscope assembly 22. In addition, the first elastic member 245 and the thread rod 242 should be located at opposite sides of a plane containing the axis 204 and perpendicular to the top surface 2211 (and the bottom surface 2212) of the rear housing portion 221 of the microscope assembly 22. With this arrangement, as shown in FIG. 8, when the Y-direction scanning knob 24 is turned to move the thread rod 242 forward, the microscope assembly 22 along with the supporting tray 25 will be pushed (against the first elastic member 245) to swing on the second axis of rotation 204 clockwise, as viewed from the side, relative to the main frame 21, thus allowing the imaging axis 201 to shift in the negative Y direction. Conversely, when the Y-direction scanning knob 24 is turned to move the thread rod 242 backward, the microscope assembly 22 along with the supporting tray 25 will be pushed down by the first elastic member 245 to swing on the second axis of rotation 204 counterclockwise relative to the main frame 21, thus allowing the imaging axis 201 to shift in the positive Y direction.

As shown in FIG. 8, when the microscope assembly 22 is aligned with the top surface 2211 perpendicular to the inner surfaces 2151,2152 of the rear portion 213 of the main frame 21, the imaging axis 201 is perpendicular to the ferrule surface 71 (i.e. the object plane 202). However, when the microscope assembly 22 is swung away from this position, the imaging axis 201 will be slightly shifted from being perpendicular to the ferrule surface 71.

In the embodiment shown FIGS. 3, 5 and 7, the first threaded through hole 2138 of the rear portion 213 of the main frame 21 is formed with a raised flange 2135 protruding outwards from the first side plate 2133 of the rear portion 213 of the main frame 21. The raised flange 2135 with the longer internal thread 2123 strengthens the connection between the thread rod 232 of the X-direction scanning knob 23 and the first threaded through hole 2138 of the rear portion 213 of the main frame 21. In the embodiment shown in FIGS. 3 and 8, the Y-direction scanning knob 24 has an outer sheath 241 with a male thread 2411 screwed to the second threaded through hole 2139 of the rear portion 213 of the main frame 21, and the thread rod 242 of the Y-direction scanning knob 24 is screwed to the threaded through hole 2414 of the outer sheath 241. In a sense, the outer sheath 241 may be considered as a raised flange formed with the threaded through hole 2414.

Figure 9:
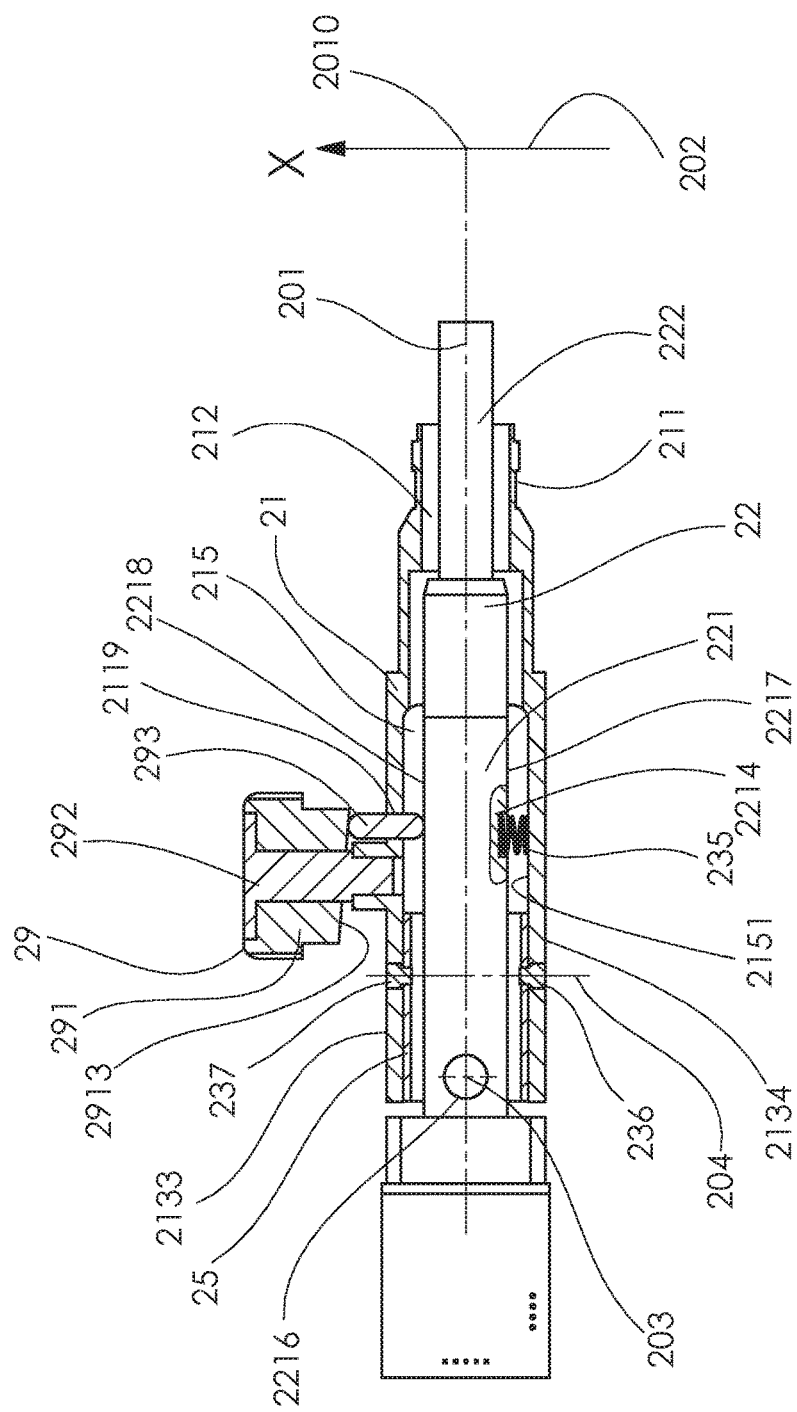
FIG. 9 shows an alternative mechanism of the scanning function in the X-direction of the connector inspector of the present invention.

FIG. 9 shows another embodiment with an alternative mechanism of the scanning function of the inspector 2 in the X-direction. In this embodiment, the X-direction scanning knob 23 described above is replaced with an X-direction scanning wheel 29 having a wheel portion 291 with a bevel surface 2913 and a cylindrical shaft 292 mounted in the first through hole 2138 of the rear portion 213 of the main frame 21, and a sliding pin 293 is movably inserted through a through hole 2119 formed in the first side plate 2133 of the rear portion 213 of the main frame 21. The sliding pin 293 contacts the bevel surface 2913 of the wheel portion 291 at one end and the second side surface 2218 of the rear housing portion 221 at an opposite end. When the wheel portion 291 of the X-direction scanning wheel 29 is turned on the cylindrical shaft 292, the bevel surface 2913 will be turned to move the sliding pin 293 relative to the through hole 2119, thus biasing the microscope assembly 22 on the first axis of rotation 203 and shifting the imaging axis 201 of the microscope assembly 22 in the X-direction.

Similarly, the mechanism of the scanning function of the inspector 2 in the Y-direction may be implemented with a Y-direction scanning wheel of a structure similar to the X-direction scanning wheel 29 illustrated in FIG. 9.

As shown in FIG. 2 and FIG. 3, the X-direction scanning knob 23 and the Y-direction scanning knob 24 are preferably disposed at about the same distance from the front end of the inspector 2. This can be accomplished by forming the first threaded through hole 2138 and the second threaded through hole 2139 at a substantially the same distance from the tubular front portion 211 of the main frame 21. In other words, the X-direction scanning knob 23 and the Y-axis scanning knob 24 are adjacently juxtaposed at 90° from each other. With this arrangement, the user may conveniently access the two scanning knobs 23,24 with the thumb and the index finger while holding the inspector 2 with other fingers of the same hand.

Further, as shown in FIG. 2 and FIG. 3, the focusing knob 27 is an annular knob disposed around the outer sheath 241 of the Y-direction scanning knob 24 such that the focusing knob 27 may be turned with the outer sheath 241 serving as the pivot. This arrangement allows the user to conveniently access each of the two scanning knobs 23,24 and the focusing knob 27 with the thumb and the index finger while holding the inspector 2 with other fingers of the same hand.

The connector inspector according to the present invention has been described above using preferred embodiments and accompanying drawings for illustrative purposes.

Therefore, the invention should not be limited to the exact structure and features shown in the accompanying drawings or the embodiments presented in the specification as various changes in the details of construction may be made without departing from the spirit of the invention.

What is claimed is:

1. An optical fiber connector inspector with two-dimensional scanning function, comprising:
    a microscope assembly having a tubular front portion and a rear housing portion, the tubular front portion having an axis collinear with an imaging axis of the microscope assembly, the rear housing portion having a top surface, a bottom surface, a first side surface and a second side surface;
    a supporting tray having two side plates and a base plate connected between respective bottom ends of the two side plates, defining a receiving space between the two side plates and above the base plate, wherein two side through holes are respectively formed in the two side plates;
    a main frame having a tubular front portion and a rear portion, the rear portion having a top plate, a first side plate, a second side plate, and a receiving space between the two side plates and below the top plate and in communication with an internal channel of the tubular front portion, wherein two side through holes are respectively formed in the two side plates;
    a fitting tip having a front insertion portion for interfacing with a fiber optic connector to be inspected and a rear portion for coupling with the tubular front portion of the main frame;
    an X-direction driving mechanism; and
    a Y-direction driving mechanism,
    wherein:
    the rear housing portion of the microscope assembly is pivoted to the base plate of the supporting tray within the receiving space of the supporting tray, such that the two side surfaces of the rear housing portion are respectively spaced from the two side plates of the supporting tray; and the microscope assembly is allowed to swing relative to the supporting tray on a first axis of rotation;
    the main frame and the supporting tray are jointed together by two pivoting joints respectively passing through the two side through holes of the rear portion of the main frame and the two side through holes of the supporting tray, such that the supporting tray and the rear housing portion of the microscope assembly are placed in the receiving space of the main frame with the tubular front portion of the microscope assembly inserted through the internal channel of the tubular front portion of the main frame and extending into the rear portion of the fitting tip; the supporting tray along with the microscope assembly is allowed to swing relative to the main frame on a second axis of rotation that extends through the two side through holes of the rear portion of the main frame, wherein the second axis of rotation is orthogonal to the first axis of rotation; and
    at least a side of the rear portion of the fitting tip has a see-through window formed thereon to allow the tubular front portion of the microscope assembly to be visible through the see-through window,
    whereby the X-direction driving mechanism interfaces with the microscope assembly for biasing the microscope assembly on the first axis of rotation relative to the main frame and therefore shifting the imaging axis of the microscope assembly in a direction perpendicular to the first axis of rotation; and
    the Y-direction driving mechanism interfaces with the microscope assembly for biasing the microscope assembly and the supporting tray on the second axis of rotation relative to the main frame and therefore shifting the imaging axis of the microscope assembly in a direction perpendicular to the second axis of rotation.

2. The optical fiber connector inspector of claim 1, wherein the first axis of rotation perpendicularly intersects the imaging axis of the microscope assembly.

3. The optical fiber connector inspector of claim 1, wherein:
    a cylindrical protrusion is formed on the bottom surface of the rear housing portion of the microscope assembly; a bottom through hole is formed in the base plate of the supporting tray; and the rear housing portion of the microscope assembly is pivoted to the base plate of the supporting tray by fittingly inserting the cylindrical protrusion into the bottom through hole in the base plate of the supporting tray.

4. The optical fiber connector inspector of claim 1, wherein:
    the X-direction driving mechanism comprises an X-direction scanning knob having a thread rod screwed into a threaded through hole in the first side plate of the rear portion of the main frame and contacting the rear housing portion of the microscope assembly, and an elastic member disposed between the second side plate of the rear portion of the main frame and the rear housing portion of the microscope assembly.

5. The optical fiber connector inspector of claim 1, wherein:
    the Y-direction driving mechanism comprises a Y-direction scanning knob having a thread rod screwed into a threaded through hole in the top plate of the rear portion of the main frame and contacting the rear housing portion of the microscope assembly, and an elastic member disposed between the top plate of the rear portion of the main frame and the rear housing portion of the microscope assembly.

6. The optical fiber connector inspector of claim 4, wherein:
    the Y-direction driving mechanism comprises a Y-direction scanning knob having a thread rod screwed into a threaded through hole in the top plate of the rear portion of the main frame and contacting the rear housing portion of the microscope assembly, and an elastic member disposed between the top plate of the rear portion of the main frame and the rear housing portion of the microscope assembly.

7. The optical fiber connector inspector of claim 4, wherein the threaded through hole in the first side plate of the rear portion of the main frame is formed with a raised flange protruding outwards from the first side plate of the rear portion of the main frame.

8. The optical fiber connector inspector of claim 5, wherein the threaded through hole in the top plate of the rear portion of the main frame is formed with a raised flange protruding outwards from the top plate of the rear portion of the main frame.

9. The optical fiber connector inspector of claim 1, wherein the second axis of rotation intersects the imaging axis of the microscope assembly.

10. The optical fiber connector inspector of claim 1, wherein a top side and a lateral side of the rear portion of the fitting tip each have a see-through window formed thereon.

11. The optical fiber connector inspector of claim 1, a top side, a bottom side, and two lateral sides of the rear portion of the fitting tip each have a see-through window formed thereon.

12. The optical fiber connector inspector of claim 1, further comprising an outer shell fixed to the main frame.

13. The optical fiber connector inspector of claim 4, wherein the elastic member has one end either attached to the first side surface of the rear housing portion, or received in a recess formed in the first side surface of the rear housing portion.

14. The optical fiber connector inspector of claim 5, wherein the elastic member has one end either attached to the top surface of the rear housing portion, or received in a recess formed in the top surface of the rear housing portion; and the first axis of rotation extends through a center of the elastic member.

15. The optical fiber connector inspector of claim 5, wherein the microscope assembly further comprises a focusing knob that has an annular shape and is disposed around the Y-direction scanning knob.

16. The optical fiber connector inspector of claim 6, wherein the threaded through hole in the first side plate and the threaded through hole in the top plate of the rear portion of the main frame are formed at a substantially the same distance from the tubular portion of the main frame.

17. The optical fiber connector inspector of claim 16, wherein the microscope assembly further comprises a focusing knob that has an annular shape and is disposed around the Y-direction scanning knob.

18. The optical fiber connector inspector of claim 1, wherein:
the X-direction driving mechanism comprises an X-direction scanning wheel having a wheel portion with a bevel surface and a cylindrical shaft mounted in a through hole in the first side plate of the rear portion of the main frame; a sliding pin passing through the first side plate of the rear portion of the main frame and contacting the bevel surface of the wheel portion at one end and the rear housing portion of the microscope assembly at another end; and an elastic member disposed between the second side plate of the rear portion of the main frame and the rear housing portion of the microscope assembly.

19. The optical fiber connector inspector of claim 1, wherein:
the Y-direction driving mechanism comprises a Y-direction scanning wheel having a wheel portion with a bevel surface and a cylindrical shaft mounted in a through hole in the top plate of the rear portion of the main frame; a sliding pin passing through the first side plate of the rear portion of the main frame and contacting the bevel surface of the wheel portion at one end and the rear housing portion of the microscope assembly at another end; and an elastic member disposed between the top plate of the rear portion of the main frame and the rear housing portion of the microscope assembly.

20. An optical fiber connector inspector with two-dimensional scanning function, comprising:
a microscope assembly having a tubular front portion and a rear housing portion, the tubular front portion having an axis collinear with an imaging axis of the microscope assembly, the rear housing portion having a top surface, a bottom surface, a first side surface and a second side surface, wherein a first recess is formed in the top surface; a second recess is formed in the first side surface; and a cylindrical protrusion is formed on the bottom surface, the cylindrical protrusion having an axis extending through the bottom surface and a center point of the first recess and perpendicularly intersecting the imaging axis of the microscope assembly;
a first elastic member having a first end received in the first recess of the rear housing portion;
a second elastic member having a first end received in the second recess of the rear housing portion;
a supporting tray having two side plates and a base plate with a top surface connected to respective bottom ends of the two side plates, defining a receiving space between the two side plates and above the base plate, wherein a bottom through hole is formed in the base plate; and two side through holes are respectively formed in the two side plates;
a main frame having a tubular front portion and a rear portion, the rear portion having a top plate, a first side plate with an inner surface, a second side plate with an inner surface, and a receiving space between the two side plates and below the top plate and in communication with an internal channel of the tubular front portion, wherein two side through holes are respectively formed in the two side plates; a first threaded through hole is formed in the first side plate; and a second threaded through hole is formed in the top plate at a point forward from the two side through holes;
a fitting tip having a front insertion portion for interfacing with a fiber optic connector to be inspected and a rear portion for coupling with the tubular front portion of the main frame;
an X-direction scanning knob having a thread rod screwed into the first threaded through hole of the rear portion of the main frame and adapted for turning the thread rod forward or backward; and
a Y-direction scanning knob having a thread rod screwed into the second threaded through hole and adapted for turning the thread rod forward or backward,
wherein:
a rear section of the rear housing portion of the microscope assembly is placed within the receiving space of the supporting tray with the bottom through hole placed rearwards relative to the two side through holes of the supporting tray, such that the two side surfaces of the rear housing portion are respectively spaced from the two side plates of the supporting tray; the cylindrical protrusion of the rear housing portion is fittingly inserted into the bottom through hole in the base plate of the supporting tray; a rear section of the bottom surface of the rear housing portion contacts the base plate of the supporting tray from above; and the microscope assembly is allowed to swing relative to the supporting tray on a first axis of rotation collinear with the axis extending through the cylindrical protrusion and the first recess of the rear housing portion;
the main frame and the supporting tray are jointed together by two pivoting joints respectively passing through the two side through holes of the rear portion of the main frame and the two side through holes of the supporting tray, such that the supporting tray and the rear housing portion of the microscope assembly are placed in the receiving space of the main frame with the tubular front portion of the microscope assembly inserted through the internal channel of the tubular front portion of the main frame and extending into the rear portion of the fitting tip; the supporting tray together with the microscope assembly is allowed to swing relative to the main frame on a second axis of rotation that is collinear with an axis extending through the two side through holes of the rear portion of the main frame; a second end of the first elastic member contacts and exerts an elastic force on the bottom surface of the top plate of the rear portion of the main frame from below; a second end of the second elastic member contacts and exerts an elastic force on the inner surface of the second side plate of the rear portion of the main frame; the thread rod of the X-direction scanning knob contacts the second side surface of the rear housing portion at a front end thereof; and the thread rod of the Y-direction scanning knob contacts the top surface of the rear housing portion at a front end thereof; and at least a side of the rear portion of the fitting tip has a see-through window formed thereon to allow the tubular front portion of the microscope assembly to be visible through the see-through window, whereby the X-direction scanning knob and the second elastic member interact with each other for biasing the microscope assembly on the first axis of rotation relative to the main frame and therefore shifting the imaging axis of the microscope assembly in a direction perpendicular to the first axis of rotation; and the Y-direction scanning knob and the first elastic member interact with each other for biasing the microscope assembly on the second axis of rotation relative to the main frame and therefore shifting the imaging axis of the microscope assembly in a direction perpendicular to the second axis of rotation.

\* \* \* \* \*